United States Patent
Takayama

(10) Patent No.: US 11,383,376 B2
(45) Date of Patent: Jul. 12, 2022

(54) BENDING MECHANISM AND MEDICAL MANIPULATOR

(71) Applicant: OLYMPUS CORPORATION, Tokyo (JP)

(72) Inventor: Hiroyuki Takayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 217 days.

(21) Appl. No.: 16/680,715

(22) Filed: Nov. 12, 2019

(65) Prior Publication Data

US 2020/0078122 A1 Mar. 12, 2020

Related U.S. Application Data

(63) Continuation of application No. PCT/JP2017/021311, filed on Jun. 8, 2017.

(51) Int. Cl.
*B25J 9/10* (2006.01)
*B25J 17/02* (2006.01)
(Continued)

(52) U.S. Cl.
CPC ............... *B25J 9/10* (2013.01); *B25J 9/107* (2013.01); *B25J 17/02* (2013.01); *B25J 17/0241* (2013.01); *F16H 35/10* (2013.01); *A61B 34/71* (2016.02)

(58) Field of Classification Search
CPC ... A61B 34/71; B25J 9/10; B25J 9/106; B25J 17/02; B25J 17/0241; B25J 19/06; F16H 35/10
See application file for complete search history.

(56) References Cited

U.S. PATENT DOCUMENTS 3,659,329 A * 5/1972 Walker ............... H02K 15/10
29/734
6,699,235 B2 * 3/2004 Wallace ............. A61B 34/70
606/1

(Continued)

FOREIGN PATENT DOCUMENTS

AU 2007231795 A1 5/2008
CA 2609492 A1 5/2008
(Continued)

OTHER PUBLICATIONS

U.S. Office Action dated Mar. 29, 2021 in U.S. Appl. No. 16/417,728.
(Continued)

*Primary Examiner* — William C Joyce
(74) *Attorney, Agent, or Firm* — Scully, Scott, Murphy & Presser, P.C.

(57) ABSTRACT

A bending mechanism includes: a support member; a pivoting member supported at a distal end of the support member to be pivotable about an axis intersecting the longitudinal axis of the support member; a link disposed along the longitudinal axis and transmitting a force applied at a proximal end thereof to cause the pivoting member to pivot; and an adjuster adjusting stresses in the link so as not to exceed a threshold, at each pivoting position of the pivoting member with respect to the support member. The link includes a first member connected to the pivoting member and a second member disposed closer to the proximal end than the first member is. The adjuster includes a movable member moving in predetermined direction when the first and second members are relatively moved, and a spring biasing the movable member in such direction as to prevent the movement of the movable member.

11 Claims, 11 Drawing Sheets

(51) Int. Cl.
*F16H 35/10* (2006.01)
*A61B 34/00* (2016.01)

(56) References Cited

U.S. PATENT DOCUMENTS

| | | | |
|---|---|---|---|
| 7,121,781 B2 * | 10/2006 | Sanchez | B25J 3/04 |
| | | | 414/1 |
| 9,101,379 B2 * | 8/2015 | Au | A61B 34/30 |
| 2007/0078456 A1 | 4/2007 | Dumbauld et al. | |
| 2007/0106297 A1 | 5/2007 | Dumbauld et al. | |
| 2008/0195144 A1 | 8/2008 | Hashimoto | |
| 2010/0204697 A1 | 8/2010 | Dumbauld et al. | |
| 2011/0196419 A1 | 8/2011 | Cooper | |
| 2012/0123441 A1 | 5/2012 | Au et al. | |
| 2012/0221146 A1 | 8/2012 | Zhang et al. | |
| 2013/0319143 A1 | 12/2013 | Huang et al. | |
| 2014/0194873 A1 | 7/2014 | Dumbauld et al. | |
| 2015/0141756 A1 | 5/2015 | Cheng et al. | |
| 2015/0289942 A1 | 10/2015 | Au et al. | |
| 2016/0038239 A1 | 2/2016 | Yamanaka et al. | |
| 2016/0135914 A1 | 5/2016 | Isoda | |
| 2016/0256183 A1 | 9/2016 | Cooper | |
| 2016/0310221 A1 | 10/2016 | Bar et al. | |
| 2017/0080581 A1 | 3/2017 | Iida et al. | |
| 2017/0304014 A1 | 10/2017 | Au et al. | |
| 2019/0183592 A1 | 6/2019 | Shelton, IV et al. | |
| 2019/0269473 A1 | 9/2019 | Takayama et al. | |
| 2020/0121343 A1 | 4/2020 | Cooper | |
| 2020/0146761 A1 | 5/2020 | Au et al. | |
| 2020/0297438 A1 | 9/2020 | Shelton, IV et al. | |

FOREIGN PATENT DOCUMENTS

| | | |
|---|---|---|
| EP | 1 913 879 A1 | 4/2008 |
| EP | 2105105 A1 | 9/2009 |
| EP | 3025669 A1 | 6/2016 |
| EP | 3159124 A1 | 4/2017 |
| JP | H06-008178 A | 1/1994 |
| JP | H06-262360 A | 9/1994 |
| JP | 2003-079638 A | 3/2003 |
| JP | 2007-044330 A | 2/2007 |
| JP | 4402313 B2 | 1/2010 |
| JP | 2012-125877 A | 7/2012 |
| JP | 2014-138879 A | 7/2014 |
| JP | 2015-23886 A | 2/2015 |
| JP | 2016-002414 A | 1/2016 |
| WO | 2011/059015 A1 | 5/2011 |
| WO | 2011/097095 A1 | 8/2011 |
| WO | 2012/064528 A1 | 5/2012 |
| WO | 2014/129362 A1 | 8/2014 |
| WO | WO 2015/012023 A1 | 1/2015 |
| WO | WO 2015/194321 A1 | 12/2015 |
| WO | WO 2018/100607 A1 | 6/2018 |

OTHER PUBLICATIONS

International Search Report dated Aug. 29, 2017 issued in PCT/JP2017/021311.
International Search Report dated Feb. 7, 2017 issued in PCT/JP2016/085313.
Japanese Office Action dated Jan. 14, 2020 in Japanese Patent Application No. 2018-553520.

* cited by examiner

US 11,383,376 B2

BENDING MECHANISM AND MEDICAL MANIPULATOR

CROSS-REFERENCE TO RELATED APPLICATIONS

This is a continuation of International Application PCT/JP2017/021311 which is hereby incorporated by reference herein in its entirety.

TECHNICAL FIELD

The present invention relates to a bending mechanism and a medical manipulator.

BACKGROUND ART

There is a known medical manipulator that includes, in a distal-end section of an elongated insertion part, a flexion joint for changing the direction of a treatment tool provided at a distal end of the medical manipulator (for example, see PTL 1).

In this medical manipulator, by pressing and pulling two links that are disposed along the insertion part and that are connected to a pivoting member located closer to the distal end than the flexion joint is, the pivoting member is made to pivot, and a treatment tool fixed to the pivoting member is made to pivot.

CITATION LIST

Patent Literature

{PTL 1} Publication of Japanese Patent No. 4402313

SUMMARY OF INVENTION

According to one aspect, the present invention provides a bending mechanism including: an elongated support member; a pivoting member that is supported at a distal end of the support member so as to be pivotable about an axis intersecting a longitudinal axis of the support member; a link that is disposed along the longitudinal axis of the support member and that transmits a driving force applied at a proximal end thereof, to cause the pivoting member to pivot with respect to the support member; and an adjuster that adjusts a stress occurring in the link so as not to exceed a predetermined threshold, at each pivoting position of the pivoting member with respect to the support member, wherein the link includes a first transmission member that is connected to the pivoting member, and a second transmission member that is disposed closer to a proximal end than the first transmission member is; and the adjuster includes a movable member that is moved in a predetermined direction when the first transmission member and the second transmission member are relatively moved in the longitudinal-axis direction, and a spring that biases the movable member in such a direction as to prevent the movement of the movable member.

DESCRIPTION OF EMBODIMENTS

A bending mechanism 5 and a medical manipulator 1 according to one embodiment of the present invention will be described below with reference to the drawings.

Figure 1:
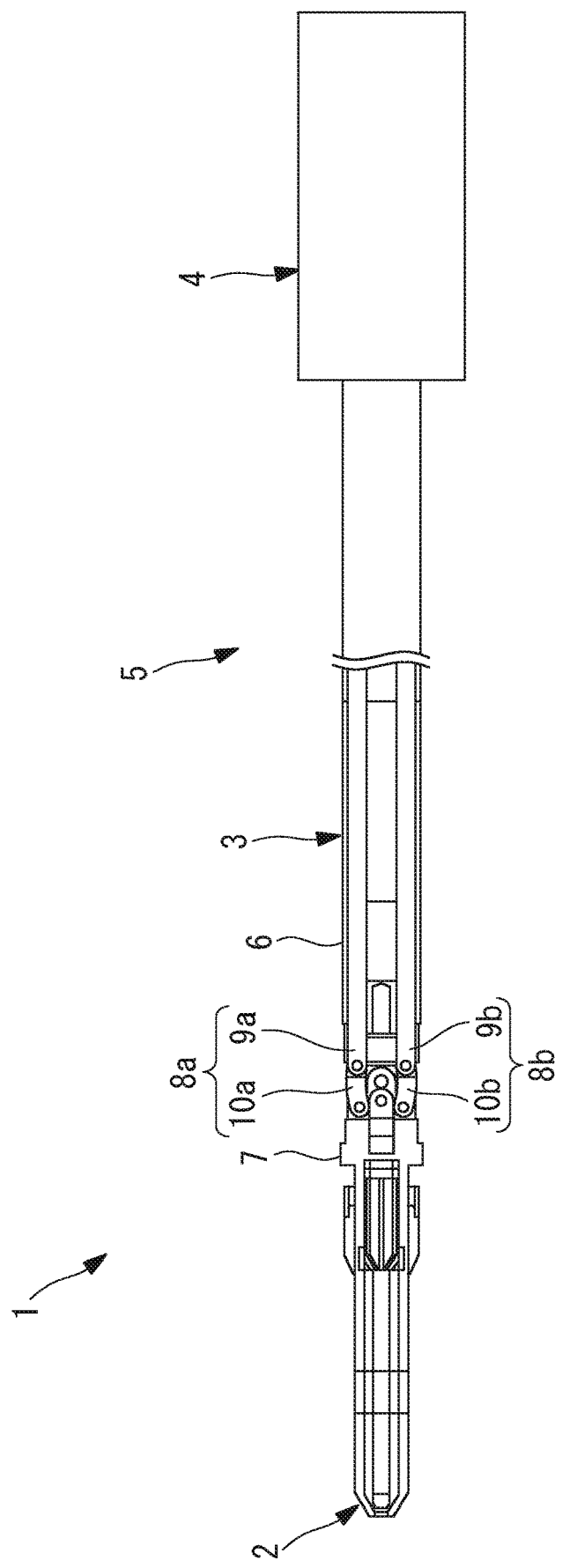
FIG. 1 is a view showing the overall configuration of a medical manipulator according to one embodiment of the present invention.

As shown in FIG. 1, the medical manipulator 1 of this embodiment includes: a treatment tool 2 that is used to treat an affected area; an elongated insertion part 3; and an operating part 4 that is connected to a proximal end of the insertion part 3. The insertion part 3 and the operating part 4 constitute the bending mechanism 5. The treatment tool 2 is mounted at a pivoting member 7 of the insertion part 3, to be described later.

As shown in FIG. 1, the insertion part 3 includes: an elongated support member 6; the pivoting member 7, which is supported at a distal end of the support member 6 so as to be pivotable about a pivot axis perpendicular to the longitudinal axis of the support member 6; and two pairs of links (driving-force transmission members) 8a and 8b that transmit a driving force applied at the operating part 4, which is located at the proximal end of the support member 6, to cause the pivoting member 7 to pivot with respect to the support member 6. The respective pairs of links 8a and 8b include: long first links (first transmission members) 9a and 9b that are disposed along the longitudinal axis of the support member 6; and short second links 10a and 10b that are coupled to the first links 9a and 9b, respectively, and to the pivoting member 7 so as to be pivotable about axes parallel to the pivot axis.

Figure 2:
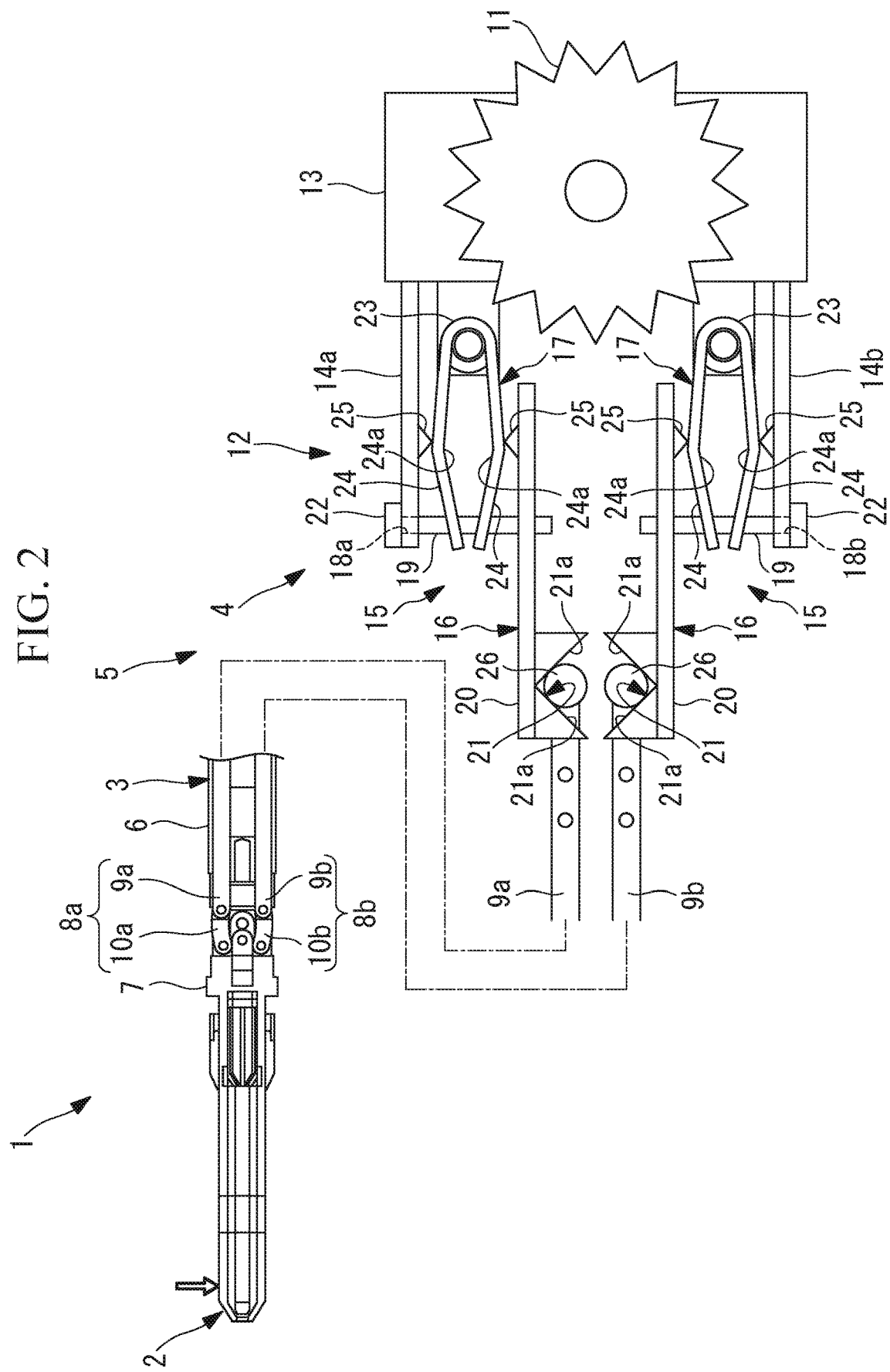
FIG. 2 is a plan view showing an operating part of the medical manipulator shown in FIG. 1.
Figure 3:
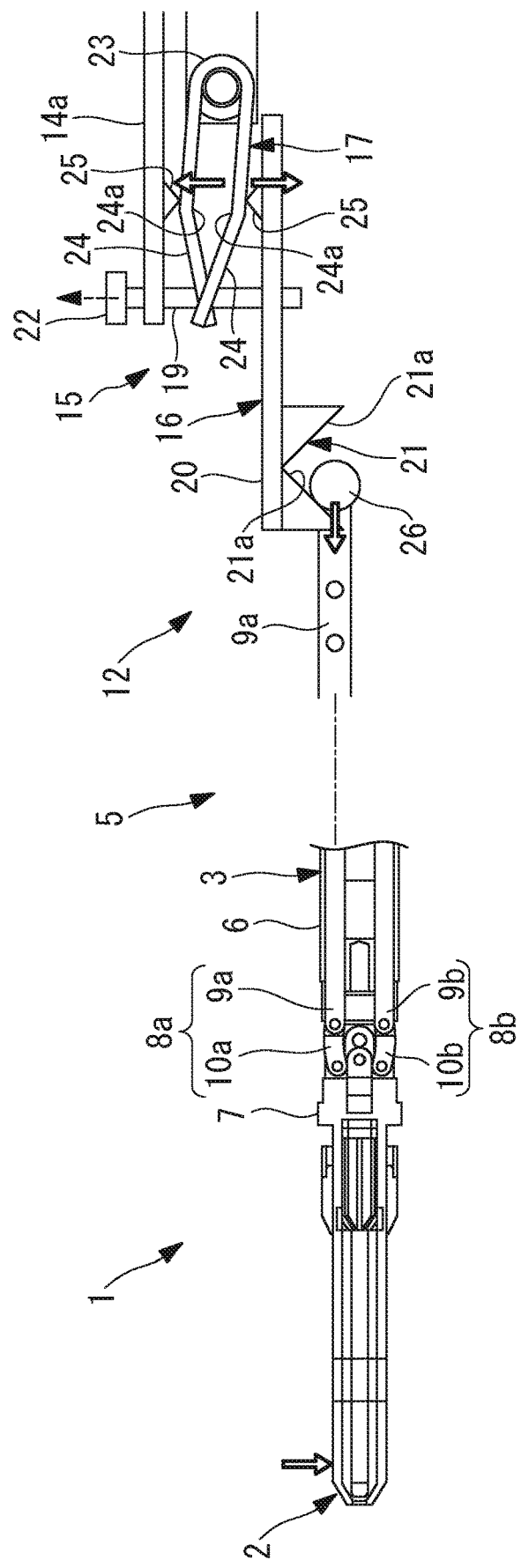
FIG. 3 is a partial plan view for explaining movement of the operating part when a predetermined external force or greater is applied to a distal end of the medical manipulator shown in FIG. 1.

As shown in FIGS. 2 and 3, the operating part 4 includes: a handle 11 that is operated by an operator and to which a driving force is applied; and a driving-force conversion part 12 that supplies the driving force, which has been applied to the handle 11, to the two pairs of links 8a and 8b.

The driving-force conversion part 12 includes: a base 13 on which the handle 11 is rotatably mounted; two third links (driving-force transmission members, second transmission members) 14a and 14b that are supported on the base 13 so as to be linearly movable in the longitudinal directions of the links 8a and 8b; rack gears (not shown) that are mounted on the third links 14a and 14b; a pinion gear (not shown) that is provided on the handle 11, that is disposed between the two parallel third links 14a and 14b, and that is engaged with the rack gears; and stress adjustment parts 15 that adjust axial forces applied to the first links 9a and 9b.

The stress adjustment parts 15 include: movable members 16 that are disposed between the first links 9a and 9b and the third links 14a and 14b and that move, when the first links 9a and 9b and the third links 14a and 14b are relatively moved in the longitudinal-axis directions of the first links 9a and 9b, in directions (predetermined directions) perpendicular to the longitudinal-axis directions; and torsion coil springs (biasing members) 17 that bias the movable members 16 in such directions as to prevent the movement of the movable members 16.

The movable members 16 include: shaft parts 19 that are fitted into through-holes 18a and 18b provided in the third links 14a and 14b and penetrating the third links 14a and 14b in directions perpendicular to the longitudinal axes of the third links 14a and 14b, so as to be movable in the axial directions of the through-holes 18a and 18b; fourth links 20 that are each fixed to one end of each of the shaft parts 19 and that extend in the longitudinal-axis directions; and V-block parts 21 that are provided at distal ends of the fourth links 20.

Stoppers 22 that have larger diameters than the through-holes 18a and 18b are provided at the other ends of the shaft parts 19. The stoppers 22 are made to abut against the third links 14a and 14b, thereby prohibiting further movement of each of the shaft parts 19 in one axial direction. Furthermore, by being inserted into the through-holes 18a and 18b, the shaft parts 19 are restricted from being moved in the longitudinal-axis directions relative to the third links 14a and 14b, and, when the third links 14a and 14b are moved in the longitudinal-axis directions, the shaft parts 19, the fourth links 20, and the V-block parts 21 are moved in the longitudinal-axis directions, together with the third links 14a and 14b.

The torsion coil springs 17 each include: a coil spring part 23; and two lever parts 24 that extend approximately in the same direction from both ends of the coil spring part 23 and that gradually expand. Each of the torsion coil springs 17 is fixed to the base 13 at the coil spring part 23 and is disposed so as to be sandwiched between a corresponding one of the third links 14a and 14b and a corresponding one of the fourth links 20 in a state in which the two lever parts 24 are elastically deformed in directions in which the two lever parts 24 come close to each other. The respective lever parts 24 include, at intermediate positions in their length directions, bent parts 24a that are bent in directions in which distal ends of the lever parts 24 come close to each other. In the torsion coil spring 17, the coil spring part 23 produces biasing forces in such directions as to separate the two lever parts 24 from each other and as to expand the space between the corresponding one of the third links 14a and 14b and the corresponding one of the fourth links 20.

Projection parts (biasing-force adjustment mechanisms) 25 that are in contact with the lever parts 24 and that press the lever parts 24 are provided at such positions on the third links 14a and 14b and the fourth links 20 as to be opposed to the lever parts 24 of the torsion coil springs 17.

Each of the V-block parts 21 includes two inclined surfaces 21a that are inclined, in opposite directions, at 45 degrees with respect to both: the direction of movement of the shaft part 19 along corresponding one of the through-holes 18a and 18b; and the longitudinal-axis direction of corresponding one of the first links 9a and 9b. The two inclined surfaces 21a are disposed to be opened in the opposite direction from the stopper 22. A cylindrical pin (cam part) 26 that is disposed at such a position as to be in contact with both of the two inclined surfaces 21a at the same time is provided at the proximal end of each of the first links 9a and 9b.

Each of the movable members 16 is constantly biased, by the biasing force of the torsion coil spring 17, at a position where the stopper 22 of the shaft part 19 abuts against a corresponding one of the third links 14a and 14b. In the state in which the pins 26 are respectively in contact with the corresponding two inclined surfaces 21a at the same time, forces applied to the third links 14a and 14b in the longitudinal-axis directions are transmitted to the first links 9a and 9b via the inclined surfaces 21a and the pins 26, thus moving the first links 9a and 9b in the longitudinal-axis directions.

Furthermore, when a large axial force acts in any one of the longitudinal-axis directions of the first links 9a and 9b, the pins 26 each press against one of the two inclined surfaces 21a, and, as a result of that, if the forces in the longitudinal directions of the shaft parts 19, the forces being produced by that pressing forces, exceed the biasing forces (thresholds) of the torsion coil springs 17, the movable members 16 are moved in the longitudinal directions of the shaft parts 19 (in such directions as to reduce the stresses). Accordingly, the pins 26 are each moved along the aforementioned one of the inclined surfaces 21a, and the first links 9a and 9b and the third links 14a and 14b are relatively moved in the longitudinal-axis directions.

Specifically, in a state in which axial forces less than a predetermined magnitude act on the first links 9a and 9b and the third links 14a and 14b, the biasing forces of the torsion coil springs 17 prevent movement of the movable members 16 and keep the first links 9a and 9b and the third links 14a and 14b from being relatively moved in the longitudinal directions, and the forces applied to the third links 14a and 14b in the longitudinal-axis directions are directly transmitted to the first links 9a and 9b. On the other hand, when axial forces of the predetermined magnitude act on the first links 9a and 9b and the third links 14a and 14b, the movable members 16 are moved against the biasing forces of the torsion coil springs 17, and the first links 9a and 9b and the third links 14a and 14b are relatively moved, thus avoiding the situation where excessive axial forces act on the first links 9a and 9b.

Figure 4:
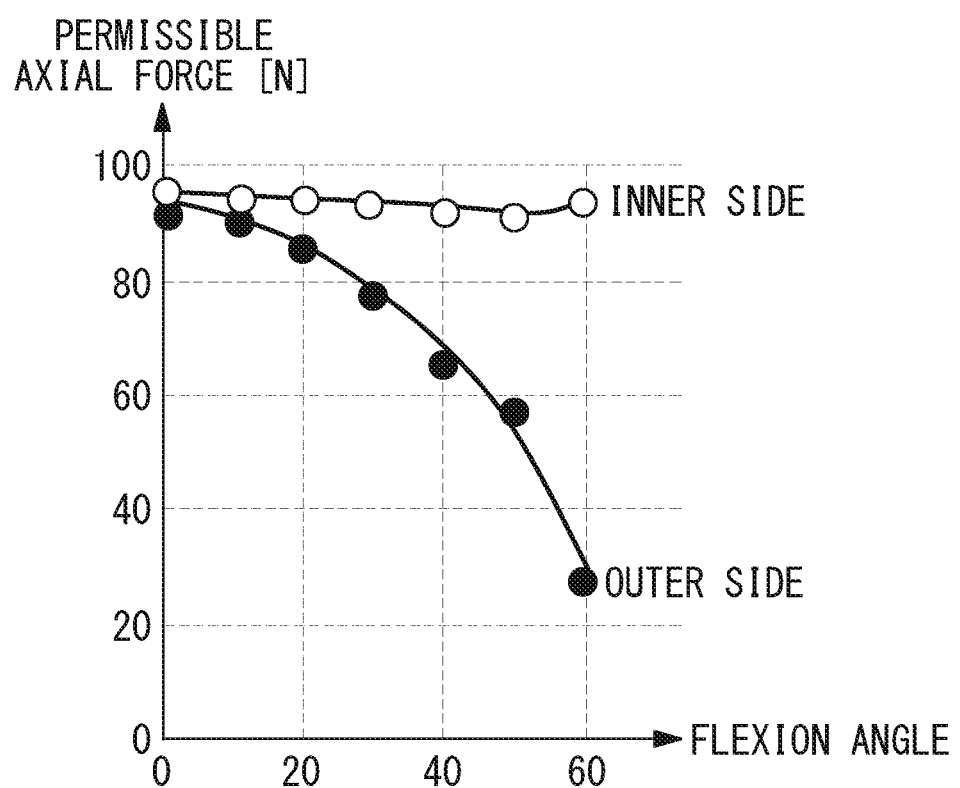
FIG. 4 is a graph showing the relationship between a flexion angle and a permissible axial force, of each of an inner-side first link and an outer-side first link of the medical manipulator shown in FIG. 1.

In this case, with the bending mechanism 5, which has the above-described configuration, as shown in FIG. 4, when the flexion angle (pivot angle) is increased at the flexion joint, there is a tendency for a permissible axial force of the first link 9a, which is located at an outer side of the flexion, to be significantly reduced, whereas a permissible axial force of the first link 9b, which is located at an inner side of the flexion, is slightly reduced.

In this embodiment, when the flexion angle is increased with reference to the position where the flexion angle is 0 degree, the contact points of the projection parts 25 and the lever parts 24 of the torsion coil spring 17 that biases the movable member 16 connected to the outer-side first link 9a are moved toward the distal end beyond the bent parts 24a of the lever parts 24, and the contact points of the projection parts 25 and the lever parts 24 of the torsion coil spring 17 that biases the movable member 16 connected to the inner-side first link 9b are moved toward the proximal end beyond the bent parts 24a of the lever parts 24.

Accordingly, when the contact points of the projection parts 25 and the lever parts 24 are moved toward the distal end beyond the bent parts 24a, because the angle between the lever parts 24 of the torsion coil spring 17 is increased, and the distances between the fulcrum and the points of action of forces from the projection parts 25 to the lever parts 24 are increased, the rigidity of the torsion coil spring 17 is significantly reduced, thus making it easy to move the movable member 16 even with a smaller force. On the other hand, when the contact points of the projection parts 25 and the lever parts 24 are moved toward the proximal end beyond the bent parts 24a, although the angle between the lever parts 24 is increased, thus reducing the rigidity of the torsion coil spring 17, the distances between the fulcrum and the points of action of forces from the projection parts 25 to the lever parts 24 are reduced, thus increasing the rigidity; therefore, the rigidity of the torsion coil spring 17 is slightly reduced as a whole.

Therefore, by appropriately changing the rigidities of the torsion coil springs 17 according to each of the positions to which the flexion angle has been changed, excessive axial forces that exceed the permissible axial forces do not act on the first links 9a and 9b.

The operation of the thus-configured bending mechanism 5 and medical manipulator 1 of this embodiment will be described below.

In order to perform treatment on an affected area by using the medical manipulator 1 of this embodiment, the insertion part 3 is inserted into the body, the treatment tool 2, which is mounted at the distal end, is disposed in the vicinity of the affected area, and the handle 11, which is provided in the operating part 4, is operated to cause the pivoting member 7 to pivot with respect to the support member 6, thereby adjusting the orientation of the treatment tool 2 with respect to the affected area.

Figure 5:
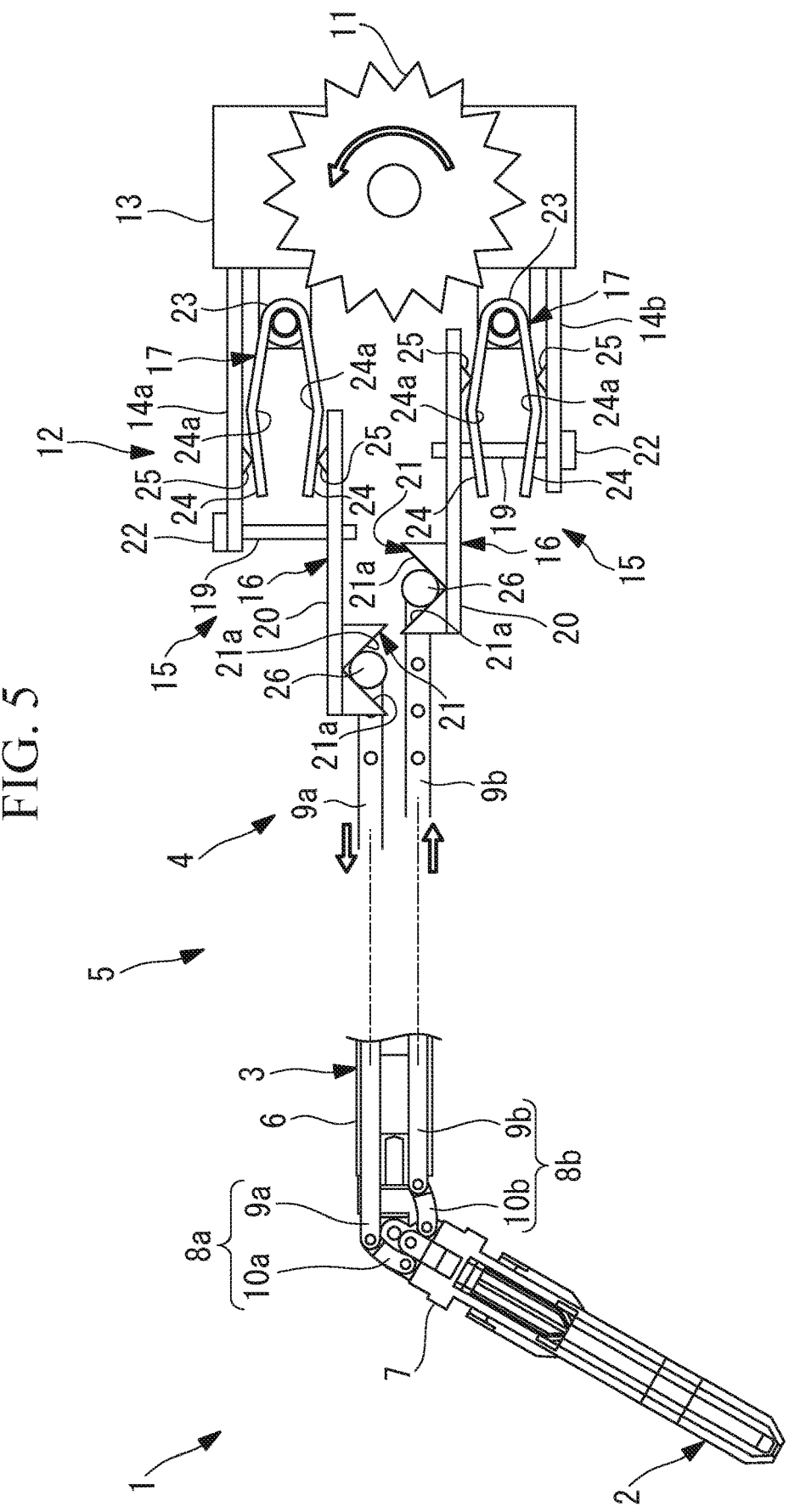
FIG. 5 is a plan view for explaining movement of the operating part of the medical manipulator shown in FIG. 1.

As shown in FIG. 5, when the handle 11 is operated so as to be rotated in one direction, the two third links 14a and 14b, which are coupled to the handle 11 via the rack gears and the pinion gear, are moved in the longitudinal-axis directions, and the pins 26 are pressed by the inclined surfaces 21a of the V-block parts 21, which are provided in the movable members 16, thereby moving the first links 9a and 9b in the longitudinal-axis directions.

Because the lever parts 24 of the torsion coil springs 17 and the projection parts 25, which are provided on the third links 14a and 14b and the fourth links 20, are formed so as to be disposed at proper relative positions according to the pivot angle of the pivoting member 7 corresponding to the rotation angle of the handle 11, the rigidities of the torsion coil springs 17 are properly set according to the pivot angle of the pivoting member 7.

Specifically, when the pivoting member 7 pivots with respect to the support member 6, as shown in FIG. 5, at the side of the first link 9a, which is located at the outer side of the flexion, the relative angle of the lever parts 24 of the torsion coil spring 17 is increased, thus significantly reducing the rigidity of the torsion coil spring 17, and, at the side of the first link 9b, which is located at the inner side of the flexion, the rigidity of the torsion coil spring 17 is slightly reduced. Accordingly, the biasing force of the torsion coil spring 17 is significantly reduced at the outer side of the flexion, and the biasing force of the torsion coil spring 17 is slightly reduced at the inner side of the flexion.

Therefore, when an external force acts on the distal end of the treatment tool 2, which is fixed to the pivoting member 7, the torsion coil spring 17 is compressed by a smaller external force at the outer side of the flexion than at the inner side of the flexion, thus making it easy to move the movable member 16 in the direction perpendicular to the longitudinal axes of the first links 9a and 9b, and the pin 26 is moved with respect to the inclined surface 21a of the V-block part 21, thus allowing relative movement of the first link 9a and the third link 14a in the longitudinal-axis directions. Although the permissible axial force of the first link 9a is significantly reduced at the outer side of the flexion, because the relative movement of the first link 9a and the third link 14a is allowed even with a small external force, there is an advantage in that it is possible to avoid the situation where an excessive axial force exceeding the permissible axial force acts on the first link 9a.

In this case, because the permissible axial force of the first link 9b is not reduced much at the inner side of the flexion, the proximal end of the first link 9b is maintained so as not to be moved by a small external force. As a result of that, it is possible to prevent damage to the first link 9a, which is located at the outer side of the flexion and of which the permissible axial force has been reduced, and to receive the external force by means of the first link 9b, which is located at the inner side of the flexion and of which the permissible axial force has not been significantly reduced.

Then, when the axial force acting on the first link 9b, which is located at the inner side of the flexion, comes close to the permissible axial force, the torsion coil spring 17 for the inner-side first link 9b is also compressed to allow relative movement of the first link 9b and the third link 14b in the longitudinal-axis directions, thus making it possible to avoid the situation where an excessive axial force exceeding the permissible axial force acts on the first link 9b. Accordingly, there is an advantage in that it is not necessary to increase the cross section of the first link 9b in view of a reduction in the permissible axial force, and to achieve a reduction in the diameter of the insertion part 3 while preventing damage.

Figure 6:
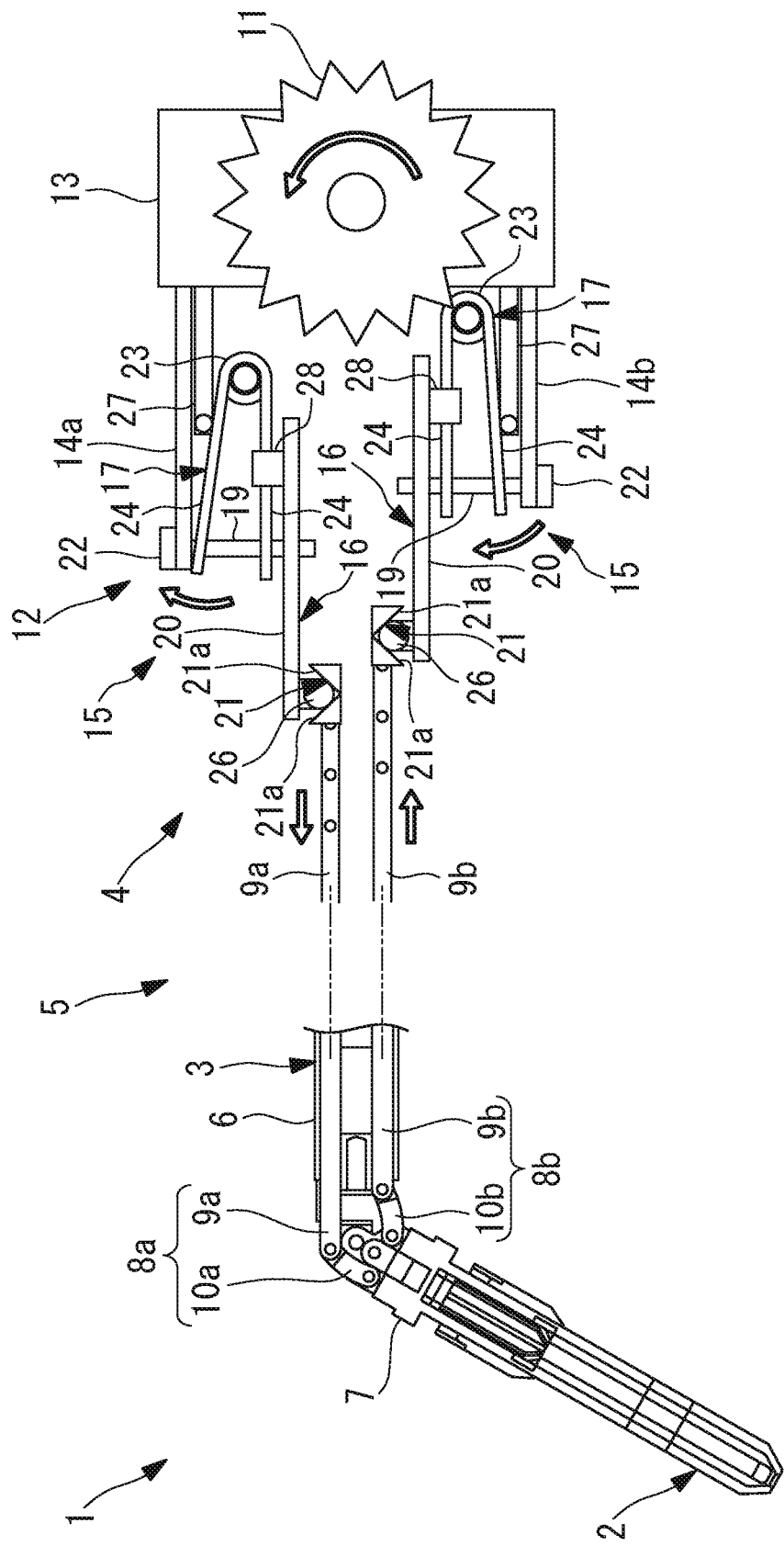
FIG. 6 is a plan view showing a first modification of the medical manipulator shown in FIG. 1.

Note that, in this embodiment, although the third links 14a and 14b and the fourth links 20 are moved with respect to the torsion coil springs 17, which are fixed to the base 13, to adjust the opening angles of the lever parts 24 of the torsion coil springs 17, thereby adjusting the rigidities appropriately according to the pivot angle of the pivoting member 7, instead of this, as shown in FIG. 6, it is also possible to fix each of the torsion coil springs 17 to the movable member 16 by means of a fixing part 28 and to fix, to the base 13, a spring pusher 27 that pushes one of the lever parts 24. Furthermore, it is also possible to provide the V-block parts 21 at the proximal ends of the first links 9a and 9b and to provide the pins 26, which abut against the inclined surfaces 21a of the V-block parts 21, on the movable members 16.

Figure 7:
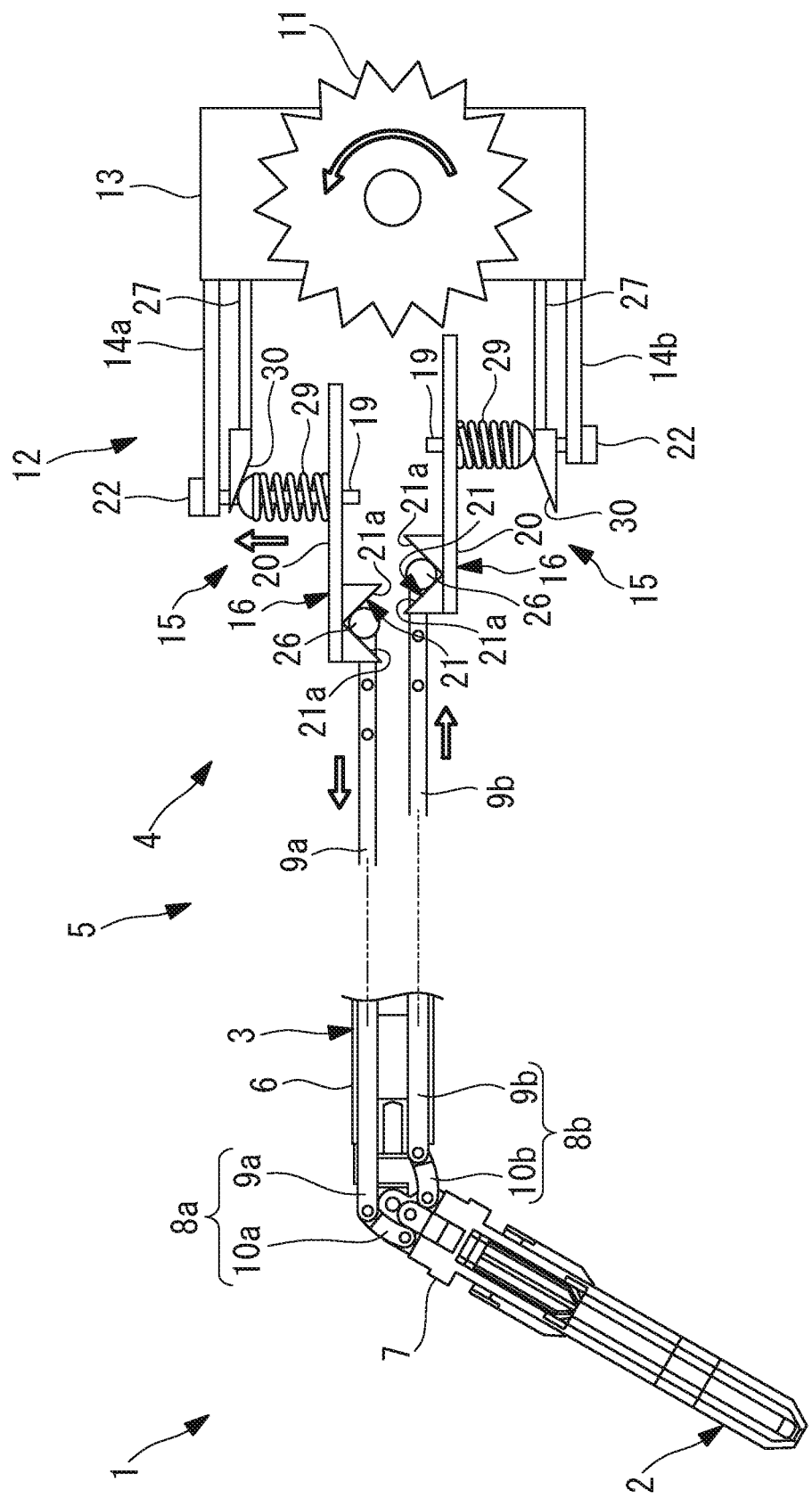
FIG. 7 is a plan view showing a second modification of the medical manipulator shown in FIG. 1.

Furthermore, instead of the torsion coil springs 17, as shown in FIG. 7, it is also possible to adopt compression coil springs (biasing members) 29. By providing slopes 30 on the spring pushers 27, it is possible to reduce the rigidity of the compression coil spring 29 at the outer side of the flexion and to increase the rigidity of the compression coil spring 29 at the inner side of the flexion.

Figure 8:
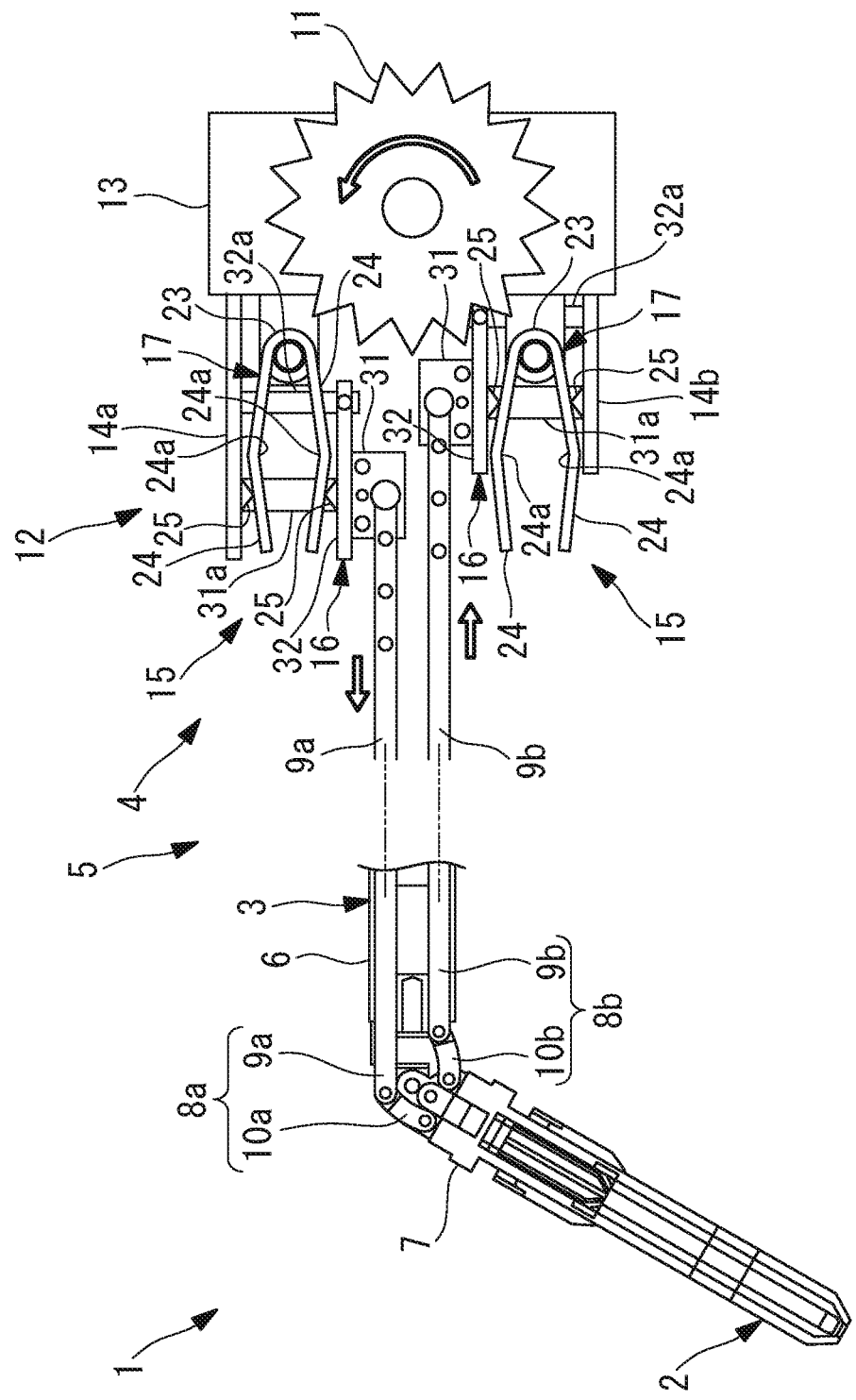
FIG. 8 is a plan view showing a third modification of the medical manipulator shown in FIG. 1.
Figure 9:
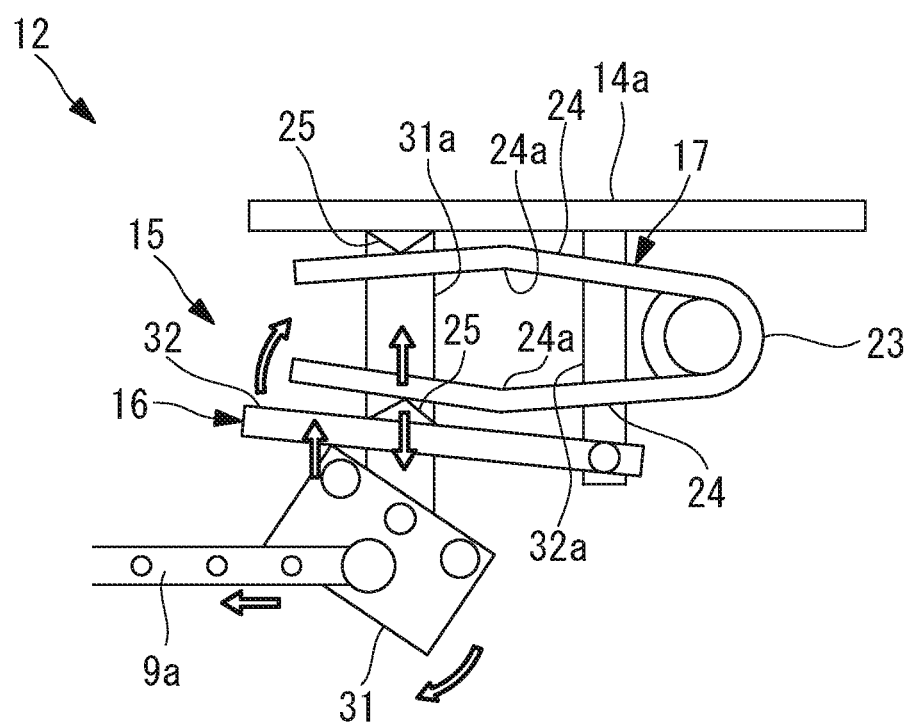
FIG. 9 is a partial plan view for explaining movement of a medical manipulator shown in FIG. 8 in one direction.

Furthermore, although a mechanism in which, when the axial force is increased, each of the movable members 16 is moved by using the pin 26 and the V-block part 21 is adopted, instead of this, as shown in FIGS. 8 and 9, it is also possible to adopt movable members 16 that include: bellcranks 31 that are provided for the third links 14a and 14b so as to be pivotable about predetermined axes and that are coupled to the proximal ends of the first links 9a and 9b at positions away from the axes; and leverage members 32 that are pivotably provided for the third links 14a and 14b and that are each made to pivot in one direction through pivoting of the corresponding bellcrank 31 in both directions. By compressing the torsion coil spring 17 in response to the pivoting of the leverage member 32, it is possible to adjust the rigidity of the torsion coil spring 17 according to the pivot angle of the pivoting member 7. FIG. 9 shows, as an example, the stress adjustment part 15 that is provided on the side of the first link 9*a*.

Specifically, as shown in FIGS. 8 and 9, in the stress adjustment parts 15, pivots of the leverage members 32 are fixed to the third links 14*a* and 14*b* by means of fixing members 32*a*, and the bellcranks 31 are provided so as to be pivotable about pivots thereof provided on fixing members 31*a* that are fixed to the third links 14*a* and 14*b*.

In a case in which the operator operates the handle 11 to move the medical manipulator 1 in one direction, for example, as shown in FIG. 8, when the handle 11 is rotated counterclockwise, the third link 14*a* is moved toward the distal end (the left side in the figure), and the third link 14*b* is moved toward the proximal end (the right side in the figure).

Accordingly, the first link 9*a* is pressed toward the distal end, as indicated by an arrow, via the bellcrank 31 that is supported by the fixing member 31*a* fixed to the third link 14*a*, whereas the first link 9*b* is pulled toward the proximal end, as indicated by an arrow, via the bellcrank 31 that is supported by the fixing member 31*a* fixed to the third link 14*b*. As a result, the pivoting member 7 is made to pivot counterclockwise.

In this case, as shown in FIG. 9, the first link 9*a* is pressed toward the distal end, the bellcrank 31 is made to pivot clockwise, thus applying a force in such a direction as to push up the leverage member 32, and the projection part 25 that is provided on the third link 14*a* and the projection part 25 that is provided on the leverage member 32 are moved toward the distal end with respect to the torsion coil spring 17, thereby changing the positions where both the projection parts 25 press the torsion coil spring 17, toward the distal end. Accordingly, when the pressing positions are moved toward the distal end of the torsion coil spring 17, in which the space becomes narrower toward the distal end, a force received by the leverage member 32 from the torsion coil spring 17 is reduced due to a reduction in the rigidity that is caused by changing the position where the force is applied, toward the distal end and due to a reduction in the rigidity that is caused by expanding the lever parts 24 of the torsion coil spring 17, thereby making it easy for the leverage member 32 to pivot with a small force.

On the other hand, the first link 9*b* is pulled toward the proximal end, the bellcrank 31 is made to pivot clockwise in FIG. 8, thus applying a force in such a direction as to push down the leverage member 32, and the projection part 25 that is provided on the third link 14*b* and the projection part 25 that is provided on the leverage member 32 are moved toward the proximal end with respect to the torsion coil spring 17, thereby changing the positions where both the projection parts 25 press the torsion coil spring 17, toward the proximal end. Accordingly, when the pressing positions are moved toward the proximal end of the torsion coil spring 17, an increase in the rigidity that is caused by changing the position where the force is applied, toward the proximal end is offset by a reduction in the rigidity that is caused by expanding the lever parts 24 of the torsion coil spring 17, thus maintaining the rigidity of the torsion coil spring 17 at a constant level.

Therefore, when an external force acts on the distal end of the treatment tool 2, the torsion coil spring 17 is compressed by a smaller external force at the outer side of the flexion than at the inner side of the flexion, and the leverage member 32 and the bellcrank 31 are made to pivot, thus making it easy to move the first link 9*a* in the longitudinal-axis direction and making it possible to avoid the situation where an excessive axial force exceeding the permissible axial force acts on the first link 9*a*.

In this case, because the permissible axial force of the first link 9*b* is not reduced much at the inner side of the flexion, the proximal end of the first link 9*b* is maintained so as not to be moved by a small external force. As a result, it is possible to prevent damage to the first link 9*a*, which is located at the outer side of the flexion and of which the permissible axial force has been reduced, and to receive the external force by means of the first link 9*b*, which is located at the inner side of the flexion and of which the permissible axial force has not been significantly reduced. Furthermore, the bellcranks 31 each act so as to push (push up or push down) the leverage member 32 in one direction, regardless of the pivot direction. Thus, even when, due to an external force acting on the distal end of the treatment tool 2, the force is applied to each of the first links 9*a* and 9*b* in any one of the directions toward the proximal end and toward the distal end, the torsion coil springs 17 can act to receive the external force.

Furthermore, in a case in which the operator rotates the handle 11 clockwise to make the medical manipulator 1 move in the other direction, the third link 14*a* is moved toward the proximal end (the right side in the figure), and the third link 14*b* is moved toward the distal end (the left side in the figure).

Accordingly, the first link 9*a* is pulled toward the proximal end via the bellcrank 31 that is supported by the fixing member 31*a* fixed to the third link 14*a*, whereas the first link 9*b* is pressed toward the distal end via the bellcrank 31 that is supported by the fixing member 31*a* fixed to the third link 14*b*. As a result, the pivoting member 7 is made to pivot clockwise.

In this case, the first link 9*a* is pulled toward the proximal end, the bellcrank 31 is made to pivot counterclockwise, thus applying a force in such a direction as to push up the leverage member 32, and the projection part 25 that is provided on the third link 14*a* and the projection part 25 that is provided on the leverage member 32 are moved toward the proximal end with respect to the torsion coil spring 17, thereby changing the positions where both the projection parts 25 press the torsion coil spring 17, toward the proximal end. Accordingly, the pressing positions are moved toward the proximal end of the torsion coil spring 17, in which the space becomes narrower toward the coil spring part 23 at the proximal end.

On the other hand, the first link 9*b* is pressed toward the distal end, the bellcrank 31 is made to pivot counterclockwise, thus applying a force in such a direction as to push down the leverage member 32, and the projection part 25 that is provided on the third link 14*b* and the projection part 25 that is provided on the leverage member 32 are moved toward the distal end with respect to the torsion coil spring 17, thereby changing the positions where both the projection parts 25 press the torsion coil spring 17, toward the distal end. Accordingly, the pressing positions are moved toward the distal end of the torsion coil spring 17.

Figure 10:
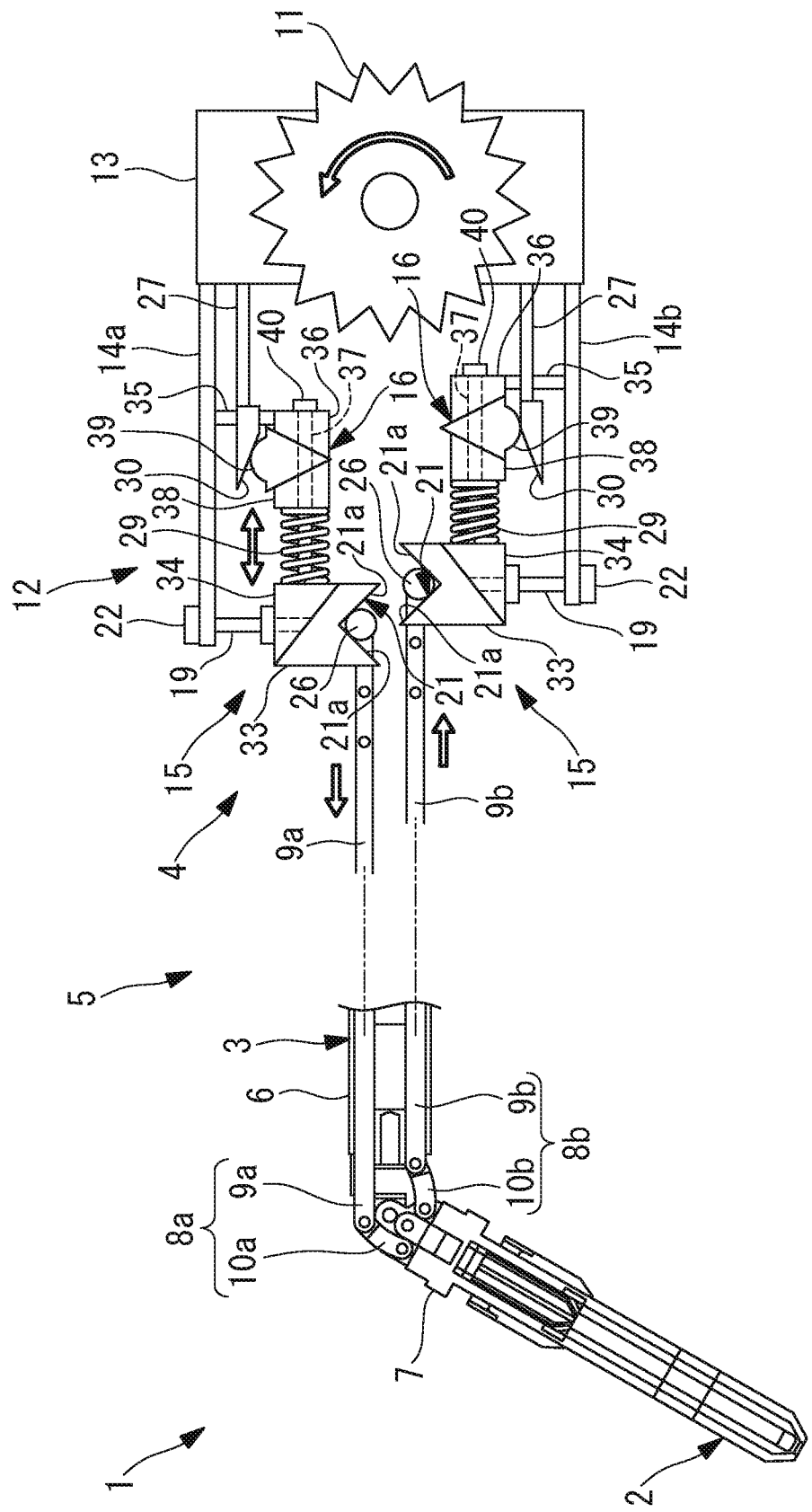
FIG. 10 is a plan view showing a fourth modification of the medical manipulator shown in FIG. 1.
Figure 11:
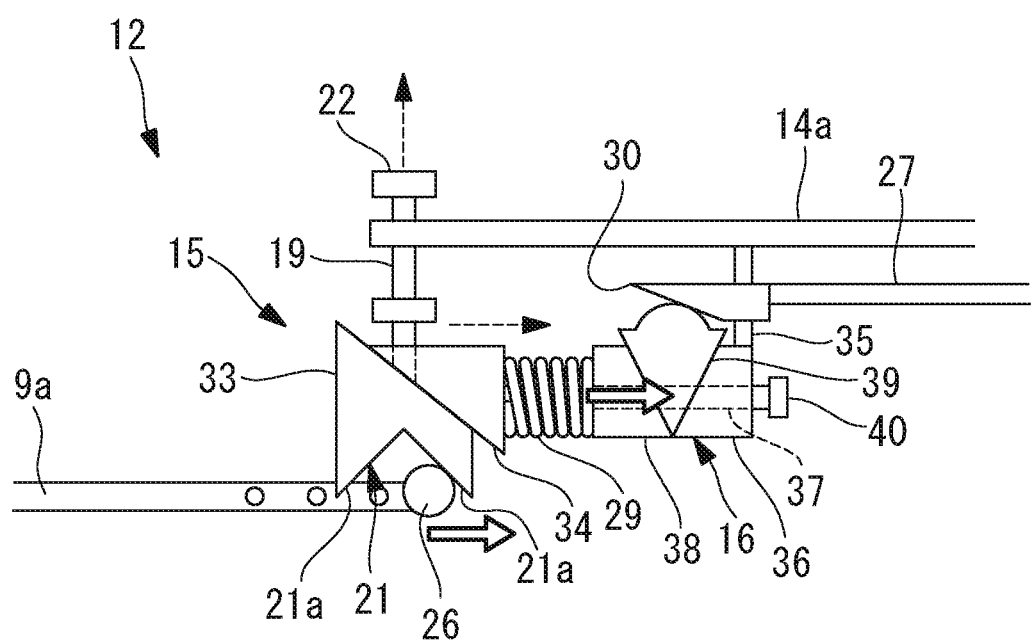
FIG. 11 is a partial plan view for explaining movement of a medical manipulator shown in FIG. 10.

Furthermore, instead of the method in which the V-block parts 21 are biased directly by the compression coil springs 29 in the directions of movement of the movable members 16, as shown in FIG. 7, it is also possible to convert the direction of movement of each of the V-block parts 21 by means of two wedge members 33 and 34 and to dispose the compression coil spring 29 in the converted direction, as shown in FIGS. 10 and 11. FIG. 11 shows, as an example, the stress adjustment part 15 that is provided on the side of the first link 9a.

Specifically, as shown in FIGS. 10 and 11, each of the stress adjustment parts 15 includes: a first wedge member 36 that is fixed to a corresponding one of the third links 14a and 14b by a fixing part 35; a shaft 37 that is disposed parallel to the corresponding one of the third links 14a and 14b and that passes through the first wedge member 36; a second wedge member 38 that is mounted, with the shaft 37 being made to pass therethrough, so as to be movable in the longitudinal direction of the shaft 37 and that has an inclined surface opposed to an inclined surface of the first wedge member 36; and a V-shaped third wedge member 39 that has two inclined surfaces and that is sandwiched between the inclined surface of the first wedge member 36 and the inclined surface of the second wedge member 38.

The third wedge member 39 is provided so as to be movable in a direction perpendicular to the longitudinal direction of the shaft 37, by making the inclined surfaces of the third wedge member 39 slide on the inclined surfaces of the first wedge member 36 and the second wedge member 38. Furthermore, when each of the third links 14a and 14b is moved in one of the front and back directions, the third wedge member 39 is moved along the inclined surface of the slope 30, which is provided on the spring pusher 27, thus being moved in a direction perpendicular to the longitudinal direction of the shaft 37.

When the third wedge member 39 is moved in the direction perpendicular to the longitudinal direction of the shaft 37, the distance between the first wedge member 36 and the second wedge member 38 in the longitudinal direction of the shaft 37 changes relatively. The wedge member 34 is fixed to a distal end of the shaft 37, a stopper 40 is provided at a proximal end of the shaft 37, and the compression coil spring 29 is disposed between the wedge member 34 and the second wedge member 38, the compression coil spring 29 biasing the second wedge member 38 in such directions as to extend the space therebetween. Furthermore, the compression coil spring 29 constantly receives a force from the second wedge member 38 in such a direction as to compress the compression coil spring 29.

The wedge members 33 are mounted at the distal ends of the third links 14a and 14b by the shaft parts 19 so as to be movable in the directions perpendicular to the longitudinal directions of the third links 14a and 14b. The wedge members 33 each include the V-block part 21, and an inclined surface of the wedge member 33 is made to be in close contact with an inclined surface of the wedge member 34.

In a case in which the operator operates the handle 11 to make the medical manipulator 1 move in one direction, for example, as shown in FIG. 10, when the handle 11 is rotated counterclockwise, the third link 14a is moved toward the distal end (the left side in the figure), and the third link 14b is moved toward the proximal end (the right side in the figure).

Accordingly, the first link 9a is pressed toward the distal end, and the third wedge member 39 is moved, along the inclined surface of the slope 30 of the spring pusher 27, in the direction (direction to come close to the third link 14a) perpendicular to the longitudinal direction of the third link 14a, thus reducing the force applied from the second wedge member 38 to the compression coil spring 29 in such a direction as to compress the compression coil spring 29. As a result of this, the first wedge member 36 and the second wedge member 38 come close to each other, thus extending the compression coil spring 29 and reducing the rigidity thereof.

Therefore, when an external force acts on the distal end of the treatment tool 2, the compression coil spring 29 is compressed by a smaller external force at the outer side of the flexion than at the inner side of the flexion, thus making it easy to move the two wedge members 33 and 34, and making it possible to avoid the situation where an excessive axial force exceeding the permissible axial force acts on the first link 9a. Furthermore, the wedge member 33 is in contact with the pin 26, on the two inclined surfaces 21a of the V-block part 21. Thus, even when, due to an external force acting on the distal end of the treatment tool 2, the force is applied to each of the first links 9a and 9b in any one of the directions toward the proximal end and toward the distal end, the compression coil springs 29 can act to receive the external force.

Furthermore, in a case in which the operator rotates the handle 11 clockwise to make the medical manipulator 1 move in the other direction, the third link 14a is moved toward the proximal end (the right side in the figure), and the third link 14b is moved toward the distal end (the left side in the figure).

Accordingly, the first link 9a is pulled toward the proximal end, and the third wedge member 39 is moved, along the inclined surface of the slope 30 of the spring pusher 27, in the direction (direction to get away from the third link 14a) perpendicular to the longitudinal direction of the third link 14a, thus increasing the force applied from the second wedge member 38 to the compression coil spring 29 in such a direction as to compress the compression coil spring 29. As a result of this, the first wedge member 36 and the second wedge member 38 are moved away from each other, thus further compressing the compression coil spring 29 and increasing the rigidity thereof.

Furthermore, in this embodiment, although the inclined surfaces 21a of the V-block part 21, which are each inclined at an angle of 45° with respect to the longitudinal-axis direction of the corresponding one of the first links 9a and 9b, are shown as an example, instead of this, it is possible to adopt inclined surfaces 21a that are inclined at an arbitrary angle. In this case, because a force applied in the direction of movement of the movable member 16 changes according to the inclination angle, the rigidity of the torsion coil spring 17 etc. needs to be designed in consideration of the force.

The above-described embodiment also leads to the following invention.

According to one aspect, the present invention provides a bending mechanism including: an elongated support member; a pivoting member that is supported at a distal end of the support member so as to be pivotable about an axis intersecting a longitudinal axis of the support member; a driving-force transmission member that is disposed along the longitudinal axis of the support member and that transmits a driving force applied at a proximal end thereof, to cause the pivoting member to pivot with respect to the support member; and a stress adjustment part that adjusts a stress occurring in the driving-force transmission member so as not to exceed a predetermined threshold, at each pivoting position of the pivoting member with respect to the support member, wherein the driving-force transmission member includes a first transmission member that is disposed close to a distal end and that is connected to the pivoting member, and a second transmission member that is disposed closer to a proximal end than the first transmission member is; and the stress adjustment part includes a movable member that is moved in a predetermined direction when the first transmission member and the second transmission member are relatively moved in the longitudinal-axis direction, and a biasing member that biases the movable member in such a direction as to prevent the movement of the movable member.

According to this aspect, when a driving force is applied to the driving-force transmission member at the proximal end of the support member, the driving force transmitted by the driving-force transmission member is transmitted to the pivoting member, and the pivoting member is made to pivot about the axis, at the distal end of the support member. In this case, through movement of the stress adjustment part, a stress that occurs in the driving-force transmission member is adjusted so as not to exceed the predetermined threshold, at each pivoting position of the pivoting member with respect to the support member.

Accordingly, even though the rigidity of the pivoting member changes according to the pivot angle, it is possible to avoid the situation where an excessive stress acts on each part. In this case, instead of achieving an increase in stress by improving the rigidities of the driving-force transmission member and respective parts, the stress itself is adjusted, thereby making it possible to prevent an increase in cross-sectional dimensions of the respective parts and to achieve a reduction in the diameter of an insertion part.

Specifically, in a state in which an excessive stress does not act on the driving-force transmission member, the movable member is maintained so as not to be moved, due to the biasing force of the biasing member, the first transmission member and the second transmission member are fixed so as not to be relatively moved, the driving force applied to the proximal end of the second transmission member is directly transmitted to the first transmission member, and the pivoting member is made to pivot. On the other hand, when an excessive stress acts on the driving-force transmission member, the movable member is moved such that the first transmission member and the second transmission member are relatively moved in the longitudinal-axis direction, against the biasing force of the biasing member. Accordingly, the stress acting on the driving-force transmission member can be relieved.

In the above-described aspect, when the stress occurring in the driving-force transmission member reaches the predetermined threshold, the stress adjustment part may allow movement of the first transmission member in such a direction as to reduce the stress.

By doing so, when a stress at a predetermined threshold occurs in the driving-force transmission member, the stress adjustment part allows movement of the first transmission member in such a direction as to reduce the stress, thus avoiding the situation where an excessive stress exceeding the predetermined threshold acts thereon.

Furthermore, in the above-described aspect, the predetermined threshold may be set to a value that differs depending on a pivot angle of the pivoting member with respect to the support member.

By doing so, in accordance with the rigidity, which changes according to the pivot angle of the pivoting member, the threshold is increased at a pivot angle at which the rigidity becomes high, and the threshold is reduced at a pivot angle at which the rigidity becomes low, thereby making it possible to prevent an excessive stress from acting on each part.

Furthermore, the above-described aspect may further include an operating part that causes the pivoting member to pivot with respect to the support member, at an angle corresponding to an operation amount, wherein the predetermined threshold may be set to a value that differs depending on the operation amount.

By doing so, in accordance with the rigidity, which changes according to the pivot angle of the pivoting member, the angle corresponding to the operation amount of the operating part, the threshold is increased at a pivot angle at which the rigidity becomes high, and the threshold is reduced at a pivot angle at which the rigidity becomes low, thereby making it possible to prevent an excessive stress from acting on each part.

Furthermore, the above-described aspect may further include a biasing-force adjustment mechanism that adjusts a biasing force produced by the biasing member, according to the operation amount.

By doing so, through adjustment of a biasing force of the biasing member performed by the biasing-force adjustment mechanism, it is possible to easily set the threshold, such that the threshold is increased at a pivot angle at which the rigidity becomes high, and the threshold is reduced at a pivot angle at which the rigidity becomes low, in accordance with the rigidity, which changes according to the pivot angle of the pivoting member.

Furthermore, in the above-described aspect, the driving-force transmission member may be able to transmit the driving force in both directions along the longitudinal axis of the support member.

By doing so, when the driving force is transmitted in both directions of the longitudinal-axis direction of the support member, the occurrence of an excessive stress can be prevented in both the directions.

Furthermore, in the above-described aspect, a cam part may be provided at a proximal end of the first transmission member; the movable member may be provided at a distal end of the second transmission member, so as to be movable in a direction perpendicular to the longitudinal axis; and the movable member may be provided with two inclined surfaces that are inclined in different directions with respect to the direction of movement of the movable member and the longitudinal axis of the support member, and against which the cam part is made to abut.

By doing so, in a state in which the movable member is not moved, the driving force is transmitted through contact between the cam part and the inclined surfaces, and, when the stress is increased to move the movable member, the contact position between the cam part and the inclined surfaces changes, thus relatively moving the first transmission member and the second transmission member in the longitudinal-axis direction, and making it possible to relieve the stress acting on the driving-force transmission member.

Furthermore, in the above-described aspect, the movable member may include: a bellcrank that is supported so as to be pivotable about a predetermined axis; and a leverage member that is made to pivot through pivoting of the bellcrank.

By doing so, through relative movement of the first transmission member and the second transmission member in the longitudinal-axis direction, the bellcrank is made to pivot in any one of the directions about the predetermined axis, and the leverage member is made to pivot in one direction through the pivoting of the bellcrank. Because the biasing member makes a biasing force act in such a direction as to prevent pivoting of the leverage member, the bellcrank is prevented from pivoting until the stress on the driving-force transmission member reaches a threshold, and, when the stress reaches the threshold, the bellcrank pivots, thus relatively moving the first transmission member and the second transmission member in the longitudinal-axis direction, and making it possible to relieve the stress acting on the driving-force transmission member.

Furthermore, according to another aspect, the present invention provides a medical manipulator including: one of the above-described bending mechanisms; and a treatment tool that is mounted on the pivoting member.

REFERENCE SIGNS LIST 1 medical manipulator
2 treatment tool
4 operating part
5 bending mechanism
6 support member
7 pivoting member
8a, 8b link (driving-force transmission member)
9a, 9b first link (first transmission member)
14a, 14b third link (second transmission member)
15 stress adjustment part
16 movable member
17 torsion coil spring (biasing member)
21a inclined surface
25 projection part (biasing-force adjustment mechanism)
26 pin (cam part)
29 compression coil spring (biasing member)
31 bellcrank
32 leverage member

The invention claimed is:

1. A bending mechanism comprising:
a support member elongated along a longitudinal axis;
a pivot supported at a distal end of the support member, the pivot being pivotable about an axis intersecting the longitudinal axis;
a link comprising a first transmission member connected to the pivot and a second transmission member disposed proximally relative to the first transmission member; and
an adjuster comprising:
a movable member configured to be movable in a first direction when the first transmission member and the second transmission member are relatively moved in a longitudinal axis direction; and
a spring configured to bias the movable member in a second direction opposing the first direction;
wherein the adjuster is configured to:
adjust a stress occurring in one or more of the first and second transmission members so as not to exceed a predetermined threshold; and
vary the predetermined threshold depending on a pivot angle of the pivot.

2. The bending mechanism according to claim 1, wherein, when the stress occurring in the link reaches the predetermined threshold, the adjuster is configured to allow movement of the first transmission member in such a direction so as to reduce the stress.

3. The bending mechanism according to claim 1, further comprising an operating part comprising a handle, the handle being configured to pivot the pivot relative to the support member, at an angle corresponding to an operation amount by the handle.

4. The bending mechanism according to claim 3, further comprising a projection configured to vary a biasing force produced by the spring, according to the operation amount.

5. The bending mechanism according to claim 1, wherein the link is a rod configured to transmit the driving force in both directions along the longitudinal axis of the support member.

6. The bending mechanism according to claim 1,
wherein a cam surface is provided on the first transmission member;
wherein the movable member comprises first and second inclined surfaces each engaged with the cam surface; and
the first and second inclined surfaces are inclined in different directions relative to the first direction and relative to the longitudinal axis.

7. The bending mechanism according to claim 1, wherein the movable member comprises:
a bellcrank pivotably supported about a predetermined axis; and
a leverage member configured to pivot through pivoting of the bellcrank.

8. A medical manipulator comprising:
the bending mechanism according to claim 1; and
a treatment tool mounted on the pivot.

9. The bending mechanism according to claim 1, wherein
a cam surface is provided at a proximal end of the first transmission member to protrude from an outer surface of the first transmission member in a direction perpendicular to the longitudinal axis;
the movable member is provided between the first transmission member and the spring; and
the spring is provided between the movable member and the second transmission member.

10. The bending mechanism according to claim 1, wherein the link is configured to transmit a driving force applied at a proximal end thereof, to cause the pivoting member to pivot with respect to the support member.

11. The bending mechanism according to claim 10, wherein
a cam surface is provided at a proximal end of the first transmission member to protrude from an outer surface of the first transmission member in a direction perpendicular to the longitudinal axis; and
the movable member is provided between the first transmission member and the spring.

* * * * *